US010311974B2

(12) United States Patent
Ding et al.

(10) Patent No.: US 10,311,974 B2
(45) Date of Patent: Jun. 4, 2019

(54) MOBILE HEALTH INTELLIGENT MEDICAL GUIDE SYSTEM AND METHOD THEREOF

(71) Applicant: Hefei University of Technology, Hefei (CN)

(72) Inventors: Shuai Ding, Hefei (CN); Shanlin Yang, Hefei (CN); Xiao Sun, Hefei (CN); Wenjuan Fan, Hefei (CN); Hang Jin, Hefei (CN); Yeqing Li, Hefei (CN); Shaowen Lan, Hefei (CN)

(73) Assignee: Hefei University of Technology, Hefei Anhui (CN)

( * ) Notice: Subject to any disclaimer, the term of this patent is extended or adjusted under 35 U.S.C. 154(b) by 0 days.

(21) Appl. No.: 15/804,033

(22) Filed: Nov. 6, 2017

(65) Prior Publication Data
US 2018/0137250 A1 May 17, 2018

(30) Foreign Application Priority Data
Nov. 15, 2016 (CN) .......................... 2016 1 1004768

(51) Int. Cl.
*G16H 50/20* (2018.01)
*G10L 15/08* (2006.01)
(Continued)

(52) U.S. Cl.
CPC ............ *G16H 50/20* (2018.01); *G10L 15/08* (2013.01); *G10L 15/22* (2013.01); *G10L 15/26* (2013.01);
(Continued)

(58) Field of Classification Search
CPC ................................. G10L 15/08; G16H 50/20
(Continued)

(56) References Cited

U.S. PATENT DOCUMENTS

| 6,915,254 B1 * | 7/2005 | Heinze .................... G06F 17/27 |
| | | 382/225 |
| 2009/0166415 A1 | 7/2009 | Braun et al. |

(Continued)

FOREIGN PATENT DOCUMENTS

| CN | 104537275 A | 4/2015 |
| CN | 104965898 A | 10/2015 |
| CN | 105512981 A | 4/2016 |

*Primary Examiner* — Hiep V Nguyen
(74) *Attorney, Agent, or Firm* — Wayne & Ken, LLC; Tony Hom (57) ABSTRACT

The present invention discloses a mobile health intelligent medical guide system and method thereof. The method comprises: collecting patient chief complaint by use of a mobile terminal, sending the patient chief complaint to a cloud server through the mobile phone device internet, analyzing and processing the patient chief complaint by use of the keyword extraction, text word segmentation, fuzzy matching and sorting recommendation technologies based on a medical knowledge base, automatically generating a disease examination result, and generating an intelligent medical guide result to be fed back to the mobile terminal in combination with the doctor information; and then optimizing the disease examination result and the intelligent medical guide result one by one until the patient ends the query or the diagnosis result achieves the optimum. The system can assist the patient to perform self-helped disease examination and medical guide in the mobile environment.

9 Claims, 4 Drawing Sheets

(51) Int. Cl.
*G10L 15/22* (2006.01)
*G10L 15/30* (2013.01)
*G10L 25/51* (2013.01)
*G10L 15/26* (2006.01)
*G16H 10/60* (2018.01)
*G06F 19/00* (2018.01)

(52) U.S. Cl.
CPC ............ G10L 15/30 (2013.01); G10L 25/51 (2013.01); *G06F 19/321* (2013.01); *G10L 2015/088* (2013.01); *G10L 2015/223* (2013.01); *G16H 10/60* (2018.01)

(58) Field of Classification Search
USPC .......................................................... 705/2
See application file for complete search history.

(56) References Cited

U.S. PATENT DOCUMENTS

| | | | |
|---|---|---|---|
| 2013/0096937 A1* | 4/2013 | Campbell | G06F 19/32 705/2 |
| 2015/0248536 A1* | 9/2015 | Tawil | G06Q 50/22 705/3 |

* cited by examiner

MOBILE HEALTH INTELLIGENT MEDICAL GUIDE SYSTEM AND METHOD THEREOF

TECHNICAL FIELD

The present invention relates to the field of mobile medical technology, and more particularly, to a mobile health intelligent medical guide system and method thereof.

BACKGROUND

With the advance of the new round of medical reform, mobile health attracts extensive attention for its convenience and high-efficiency. Mobile health is based on mobile communication technology, and provides medical services and promotes communication between doctors and patients through the mobile Internet. Mobile health not only can save a lot of registration and queuing time, but also can better solve problems such as the difficulty and high cost of getting medical treatment caused by the uneven distribution of quality medical resources. In recent years, mobile medical technology has received all attention of the academia and industry, related medical, information, communication and other technologies are becoming mature, but the following defects still exist:

1. the existing mobile medical products are conducive to simplify the patient treatment process, but still fails to achieve the intelligent auxiliary function for the self-determination of patient's condition; and 2. for the existing mobile medical products, the patient mostly subjectively selects a doctor in combination with personal experience, lacking effective integration of doctors attending, professional experience, historical evaluation and other information, which results in that the quality of mobile medical services cannot be guaranteed.

SUMMARY

The present invention is directed to overcoming the shortcomings of the prior art and to provide a mobile health intelligent medical guide system and method thereof, which is capable of assisting a patient to autonomously diagnose the condition quickly and accurately and recommending a suitable doctor for mobile diagnosis and treatment. The present invention can effectively save the patient's treatment time, improve the quality of treatment services and save the mobile medical service resources.

The present invention adopts the following technical solution for solving the technical problem:

A mobile health intelligent medical guide system of the present invention is characterized in that it comprises a mobile medical terminal and a mobile medical cloud server.

The mobile medical terminal comprises a voice recognition module, a text entry module and a mobile medical cloud server connection interface.

The mobile medical cloud server comprises a medical knowledge base, a knowledge reasoning module and a data management module.

The voice recognition module is used to acquire a patient voice chief complaint, convert it into a text chief complaint, and then send the text chief complaint to the mobile medical cloud server through the mobile medical cloud server connection interface.

The text entry module is used to manually input the text chief complaint and send it to the mobile medical cloud server through the mobile medical cloud server connection interface.

The knowledge reasoning module in the mobile medical cloud server receives the text chief complaint and obtains a disease diagnosis result and a decision result by use of the medical knowledge base to perform knowledge reasoning to the text chief complaint.

The data management module matches a corresponding treatment doctor from the medical knowledge base according to the disease diagnosis result so as to generate a medical guide result and feeds back the medical guide result to the mobile medical terminal through the mobile medical cloud server connection interface; and meanwhile, generates reminder information for supplementing the chief complaint according to the decision result.

The mobile health intelligent medical guide system according to the present invention is also characterized in that the medical knowledge base comprises a medical data index, a clinical information table, a disease information table, a doctor information table and a department information table.

The clinical information table comprises electronic medical records and medical image data.

The disease information table comprises disease number, disease name, department number, disease profile, clinical presentation and treatment.

The medical data index is an index established for the disease information table and the clinical information table.

The doctor information table comprises doctor number, doctor name, hospital, department number and professional good.

The department information table comprises department number, department name and disease number.

The knowledge reasoning module comprises a medical text word segmentation processor, a medical text stop words list, a fuzzy matching processor, an intelligent sorting processor and an optimization decision processor including an optimal rule set.

The medical text word segmentation processor performs word segmentation on the information in the clinical information table and the disease information table to obtain the clinical information table and disease information table with performance of the word segmentation.

The mobile medical cloud server removes the stop words from the clinical information table and disease information table with performance of the word segmentation based on the medical text stop words list to obtain the clinical information table and disease information table with removal of the stop words.

The mobile medical cloud server removes the stop words from the text chief complaint based on the medical text stop words list, thereby obtaining keywords of the text chief complaint.

The fuzzy matching processor uses a fuzzy matching algorithm and the medical data index to fuzzily match the keywords of the text chief complaint and the clinical information table and disease information table with removal of the stop words so as to obtain a preliminary disease diagnosis result.

The intelligent sorting processor performs a correlation estimation on the preliminary disease diagnosis result to obtain a scoring result, intelligently sorts the scoring result to obtain a sorting result, and takes the top N pieces of data from the sorting result as a disease diagnosis result.

The optimization decision processor performs an optimization decision on the disease diagnosis result by use of the optimal rule set, and if the disease diagnosis result satisfies any one of the rules of the optimal rule set, the disease diagnosis result is optimal, and thus the decision result is "True"; otherwise, it means that the disease diagnosis result is not optimal, and thus the decision result is "False".

The data management module comprises a data extraction module and a doctor scoring module.

According to the disease diagnosis result, the data extraction module selects the matched disease number, disease name, department number and disease profile from the disease information table by use of the medical data index; and obtains the doctor name and the hospital from the doctor information table according to the department number so as to obtain a number of treatment doctors.

The doctor scoring module scores and sorts the number of the treatment doctors, and selects the top M treatment doctors in ranking as the medical guide result.

A mobile health intelligent medical guide method according to the present invention is characterized in that it comprises following steps:

Step 1, establishing a medical knowledge base, wherein the medical knowledge base comprises a medical data index, a clinical information table, a disease information table, a doctor information table and a department information table, wherein, the clinical information table comprises electronic medical records and medical image data;

the disease information table comprises disease number, disease name, department number, disease profile, clinical presentation and treatment;

the medical data index is an index established for the disease information table and the clinical information table;

the doctor information table comprises doctor number, doctor name, hospital, department number and professional good; and the department information table comprises department number, department name and disease number;

Step 2, performing word segmentation on the information in the clinical information table and the disease information table to obtain the clinical information table and disease information table with performance of the word segmentation;

Step 3, removing the stop words from the clinical information table and disease information table with performance of the word segmentation based on the medical text stop words list to obtain the clinical information table and disease information table with removal of the stop words;

Step 4, obtaining a patient chief complaint by way of voice or text;

Step 5, removing the stop words from the patient chief complaint to obtain keywords of the text chief complaint;

Step 6, using a fuzzy matching algorithm and the medical data index to fuzzily match the keywords of the text chief complaint and the clinical information table and disease information table with removal of the stop words so as to obtain a preliminary disease diagnosis result;

Step 7, performing a correlation estimation on the preliminary disease diagnosis result to obtain a scoring result, intelligently sorting the scoring result to obtain a sorting result, and taking the top N pieces of data from the sorting result as a disease diagnosis result;

Step 8, performing an optimization decision on the disease diagnosis result to obtain a decision result, and generating reminder information for supplementing the chief complaint according to the decision result;

Step 9, selecting the matched disease number, disease name, department number and disease profile from the disease information table by use of the medical data index according to the disease diagnosis result, and obtaining the doctor name and the hospital from the doctor information table according to the department number so as to obtain a number of treatment doctors; and Step 10, scoring and sorting the number of the treatment doctors, and selecting the top M treatment doctor in ranking as a medical guide result.

Compared with the prior art, the present invention has the advantages that:

1. For the mobile health intelligent medical guide system of the present invention, the mobile medical terminal is installed on a personal mobile device, so that a patient can enter his/her own symptoms in a strange environment to be transmitted to a mobile medical cloud server, and the system integrates a voice input function, wherein the cloud server can analyze symptoms according to the symptom description of the patient and return the diagnosis result and medical guide result to the personal mobile device, so that the disease condition can be quickly diagnosed and an appropriate doctor can be recommended.

2. The mobile health intelligent medical guide system of the present invention establishes a medical knowledge base comprising medical knowledge, clinical guideline, doctor and hospital information by use of a cloud storage technology, for fuzzy matching and doctor retrieval recommendation, so that a patient can access to the system in the mobile Internet environment without the geographical restrictions.

3. For the mobile health intelligent medical guide system of the present invention, the knowledge reasoning module adopts a text word segmentation technique, a text stop words removal technique, a fuzzy matching method and a TF-IDF algorithm, so as to quickly and effectively diagnose the disease condition according to the symptom description of the patient and produce the disease diagnosis result, and meanwhile, to decide whether the diagnosis result is optimal according to the optimal rule set and to guide the patient to supplement the symptom description according to the optimization decision result, thereby improving the efficiency and accuracy of disease diagnosis.

4. For the mobile health intelligent medical guide system of the present invention, the data management module uses a database technology and thus can quickly extract the disease diagnosis result, simultaneously extract relevant doctors according to the relationship of the disease-department-doctor, and score and sort the doctors according to information relevant to the doctors, thereby recommending an appropriate doctor to the patient.

5. In the mobile health intelligent medical guide method of the present invention, the patient text chief complaint is acquired from a personal mobile terminal device (if the chief complaint is the voice chief complaint, it is converted into the text chief complaint), the text chief complaint is transmitted to the mobile medical cloud server by use of an interface, the mobile medical cloud server automatically gives a diagnosis according to the patient chief complaint, generates a medical guide result according to the disease diagnosis result, can guide the patient to continue to supplement the chief complaint if the disease diagnosis result is not optimal, so as to make the disease diagnosis result more accurate through multiple iterations.

DESCRIPTION OF THE EMBODIMENTS

Figure 1:
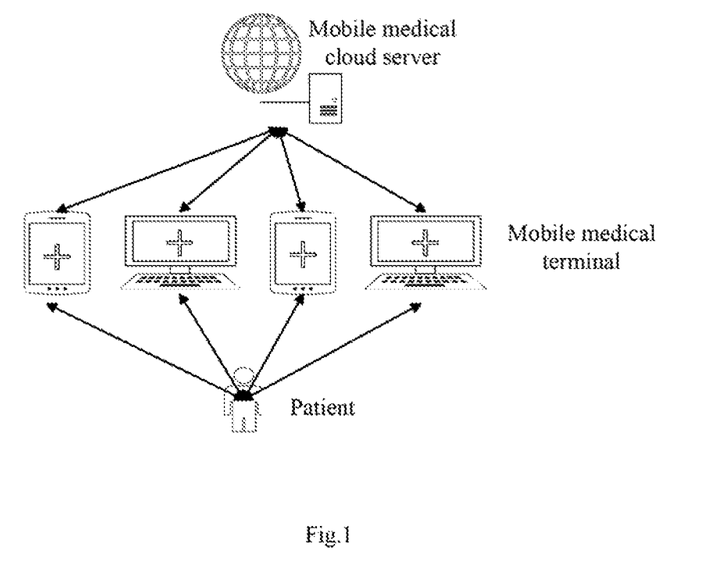
FIG. 1 is a structure schematic diagram of a system according to the present invention.

In an embodiment, a mobile health intelligent medical guide system as shown in FIG. 1 comprises a mobile medical terminal and a mobile medical cloud server.

Figure 2:
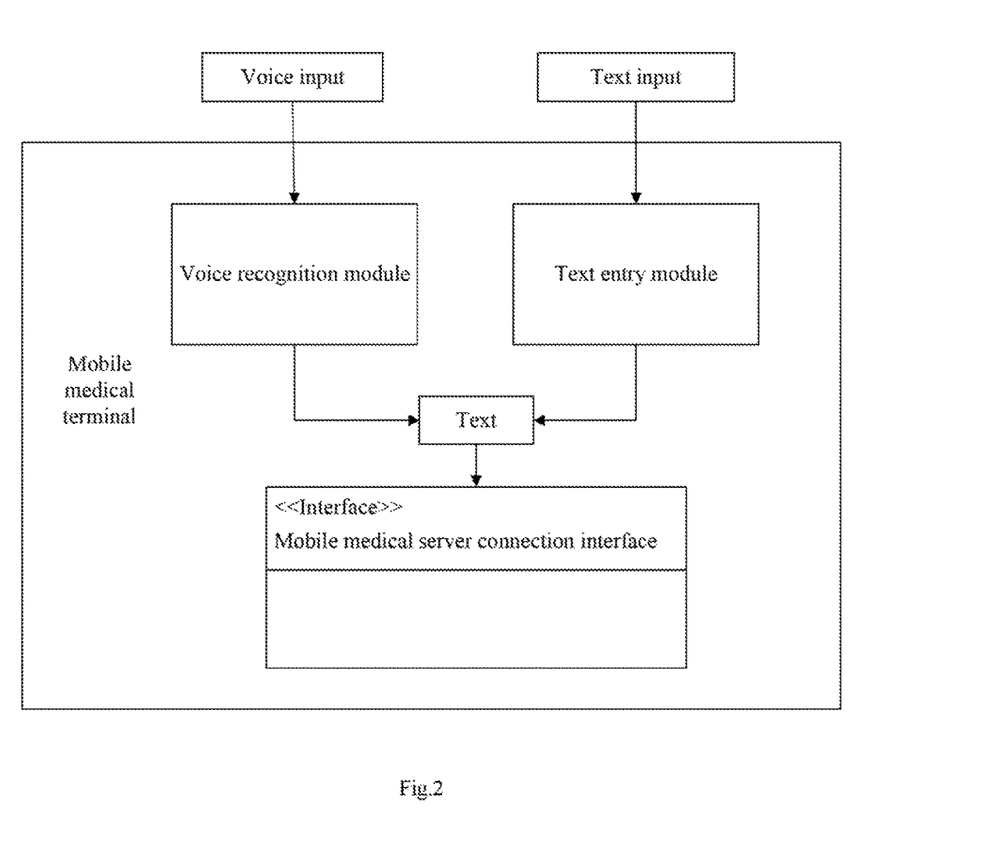
FIG. 2 is a structure schematic diagram of a mobile medical terminal according to the present invention.

The mobile medical terminal is a terminal application installed on a mobile terminal, such as a smart phone, a tablet PC and a hospital medical guide desk, is mainly used to collect a patient chief complaint and converts the patient chief complaint into text to be sent to the mobile medical cloud server, and then processes and displays a diagnosis result and a medical guide result returned by a mobile medical cloud server interface. As shown in FIG. 2, the mobile medical terminal comprises a voice recognition module, a text entry module, a mobile medical cloud server connection interface.

Figure 3:
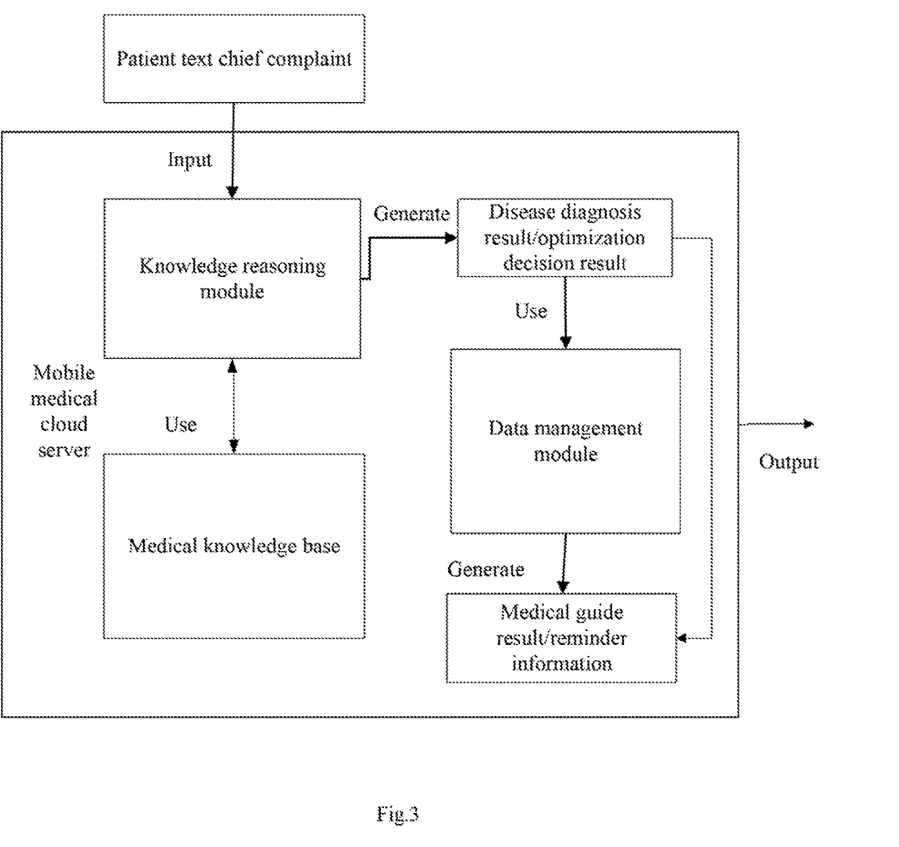
FIG. 3 is a structure schematic diagram of a mobile medical cloud server according to the present invention.

The mobile medical cloud server is a server system configured on a cloud-side server, is mainly used to generate the diagnosis result and the medical guide result by performing intelligent analysis according to the patient chief complaint transmitted by the mobile medical cloud server interface, and sends the diagnosis result and the medical guide result through the mobile medical cloud server interface. As shown in FIG. 3, the mobile medical cloud server comprises a medical knowledge base, a knowledge reasoning module and a data management module.

The voice recognition module is used to acquire a patient voice chief complaint and convert it into a text chief complaint, and then send the text chief complaint to the mobile medical cloud server through the mobile medical cloud server connection interface.

The text entry module is used to manually input the text chief complaint and send it to the mobile medical cloud server through the mobile medical cloud server connection interface.

The knowledge reasoning module in the mobile medical cloud server receives the text chief complaint and obtains a disease diagnosis result and a decision result by use of the medical knowledge base to perform knowledge reasoning to the text chief complaint.

The data management module matches a corresponding treatment doctor from the medical knowledge base according to the disease diagnosis result so as to generate a medical guide result and feeds back the medical guide result to the mobile medical terminal through the mobile medical cloud server connection interface; and meanwhile, generates reminder information for supplementing the chief complaint according to the decision result.

Figure 4:
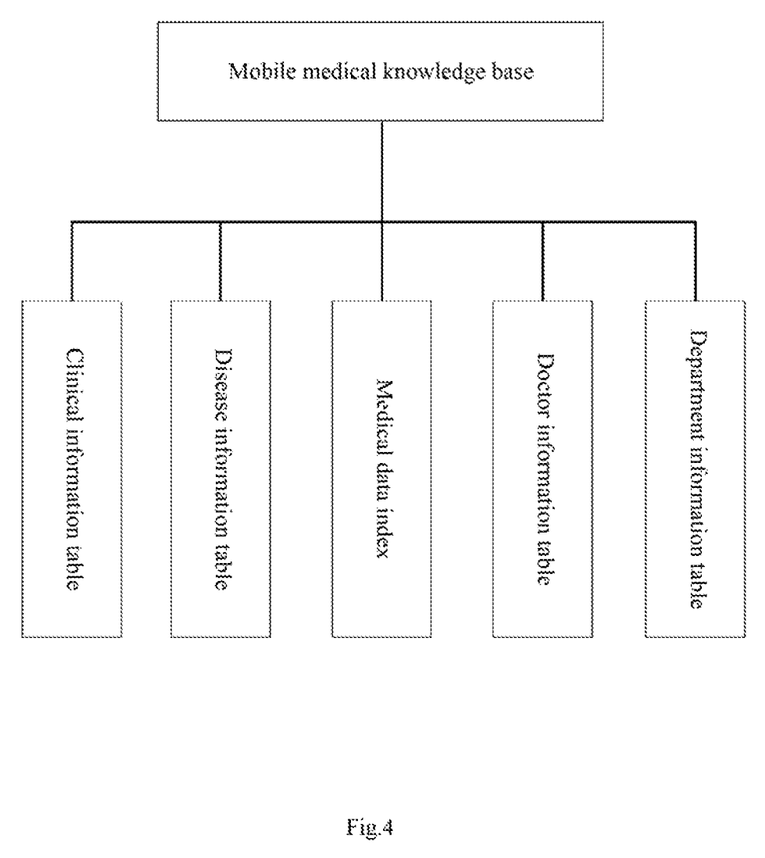
FIG. 4 is a structure schematic diagram of a mobile medical knowledge base in the mobile medical cloud server according to the present invention.

Wherein, the medical knowledge base contains clinical information, disease information and department information needed for knowledge reasoning, doctor information needed for medical guide, as well as an index established in order to improve the efficiency of the knowledge reasoning and medical guide information search. As shown in FIG. 4, the medical knowledge base comprises a medical data index, a clinical information table, a disease information table, a doctor information table and a department information table.

The clinical information table comprises electronic medical records and medical image data.

The disease information table comprises disease number, disease name, department number, disease profile, clinical presentation and treatment.

The medical data index is an index established for the disease information table and the clinical information table.

The doctor information table comprises doctor number, doctor name, hospital, department number and professional good.

The department information table comprises department number, department name and disease number.

The knowledge reasoning module firstly preprocesses the clinical information table and the disease information table, then acquires keywords of the patient chief complaint, and finally fuzzily matches the keywords of the patient chief complaint and the processed disease information table so as to obtain a matching result to be screened. The knowledge reasoning module comprises a medical text word segmentation processor, a medical text stop words list, a fuzzy matching processor, an intelligent sorting processor and an optimization decision processor including an optimal rule set, and the specific method thereof is as follows:

Before the knowledge reasoning, firstly, the medical text word segmentation processor performs word segmentation on the electronic medical records in the clinical information table and the disease profile, clinical presentation and treatment in the disease information table to obtain the clinical information table and disease information table with performance of the word segmentation; then, the mobile medical cloud server removes the stop words from the electronic medical records in the clinical information table and the disease profile, clinical presentation and treatment in the disease information table with performance of the word segmentation based on the medical text stop words list, to obtain the clinical information table and disease information table with removal of the stop words;

After the mobile medical cloud server receives the text chief complaint, the mobile medical cloud server removes the stop words from the text chief complaint based on the medical text stop words list, thereby obtaining keywords of the text chief complaint;

The fuzzy matching processor uses a fuzzy matching algorithm and the medical data index to fuzzily match the keywords of the text chief complaint and the electronic medical records in the clinical information table and the disease profile, clinical presentation and treatment in the disease information table with removal of the stop words, so as to obtain a preliminary disease diagnosis result;

The intelligent sorting processor performs a correlation scoring on the preliminary disease diagnosis result to obtain a scoring result through the TF-IDF algorithm and the BM25 scoring method, but the method is not only limited to these algorithms, then intelligently sorts the scoring result to obtain a sorting result, and takes the top N pieces of data from the sorting result as a disease diagnosis result, wherein the specific implementation steps of applying the TF-IDF algorithm are as follows:

1) For the keyword $t_i$ of the patient chief complaint, its term frequency (TF) is:

$$tf_{i,j} = \frac{n_{i,j}}{\sum_k n_{k,i}},$$

wherein $n_{i,j}$ is the number of occurrence of the keywords in the diagnosis result $d_j$, and the denominator is the sum of the number of the occurrence of all words in the diagnosis result $d_j$;

2) For the keyword $t_i$ of the patient chief complaint, its inverse document frequency (IDF) is $$idf_i = \log \frac{|D|}{|\{j:t_i \in d_j\}|},$$

wherein |D| represents the total number of diseases in the electronic medical records of the clinical information table and the disease information table, and $|j:t_i \Box d_j|$ represents the number of diseases of the preliminary diagnosis result, and if the number of the diseases of the preliminary diagnosis result is 0, it is expressed as $1+|j:t_i \Box d_j|$;

3) The correlation of the keyword $t_i$ in the diagnostic result $d_j$ is: $tfidf_{i,j}=tf_{i,j} \times idf_i$;

4) The result of the correlation scoring is sorted in descending order and the top N pieces of data are taken as the disease diagnosis result.

The optimization decision processor performs a optimization decision on the disease diagnosis result by use of the optimal rule set, and if the disease diagnosis result satisfies any one of the rules of the optimal rule set, the disease diagnosis result is optimal, and thus the decision result is "True"; otherwise, it means that the disease diagnosis result is not optimal, and thus the decision result is "False", wherein the optimal rule set comprises a number rule and a scoring rule, but the optimal rule set is not only limited to these rules. The specific implementation steps thereof are as follows:

1) The number rule: if there is only one disease diagnosis result, the diagnosis result is taken as being optimal, and the optimal decision result is "True";

2) the scoring rule: setting a threshold $\alpha$, making the correlation scoring of the first diagnostic result after being sorted is G1, and making the correlation scoring of the second diagnostic result after being sorted is G2, wherein if G1−G2>$\alpha$, the diagnosis result is taken as being optimal, and the optimal decision result is "True";

3) If the disease diagnosis result does not satisfy any one of the rules of the optimal rule set, it means that the disease diagnosis result is not optimal, so that the optimal decision result is "False";

Wherein, the data management module comprises a data extraction module and a doctor scoring module.

According to the disease diagnosis result, the data extraction module selects the matched disease number, disease name, department number and disease profile from the disease information table by use of the medical data index; and obtains the doctor name and the hospital from the doctor information table according to the department number so as to obtain a number of treatment doctors.

The doctor scoring module scores and sorts the correlation between professional good of the number of the treatment doctors and the disease diagnosis result, and selects the top M treatment doctors in ranking as the medical guide result.

The data management module generates reminder information according to the optimal decision result, wherein if the optimal decision result is "True", the reminder information "diagnosis ends" is generated, and if the optimal decision result is "False", the reminder information "in order to improve the accuracy, please supplement the chief complaint information" is generated; and send the disease diagnosis result, the medical guide result and the reminder information together to the mobile medical terminal.

In an embodiment, a mobile health intelligent medical guide method is provided, comprising: acquiring a patient chief complaint by use of a mobile terminal, sending the patient chief complaint to a cloud-side server via mobile Internet, analyzing and processing the patient chief complaint by use of the keyword extraction, text word segmentation, fuzzy matching and sorting recommendation technologies based on a medical knowledge base, automatically generating a disease examination result, and generating an intelligent medical guide result to be fed back to the mobile terminal in combination with the doctor information; and reminding the patient to supplement the chief complaint information by use of an intelligent guide mode if the patient does not end this query or the diagnosis result does not achieve the optimum, and then optimizing the disease examination result and the intelligent medical guide result one by one until the patient ends the query or the diagnosis result achieves the optimum. Specifically, the method comprises the following steps:

Step 1, establishing a medical knowledge base, wherein the medical knowledge base comprises a medical data index, a clinical information table, a disease information table, a doctor information table and a department information table, wherein, the clinical information table comprises electronic medical records and medical image data;

the disease information table comprises disease number, disease name, department number, disease profile, clinical presentation and treatment;

the medical data index is an index established for the disease information table and the clinical information table;

the doctor information table comprises doctor number, doctor name, hospital, department number and professional good; and the department information table comprises department number, department name and disease number;

Step 2, performing word segmentation on the information in the clinical information table and the disease information table to obtain the clinical information table and disease information table with performance of the word segmentation;

Step 3, removing the stop words from the clinical information table and disease information table with performance of the word segmentation based on the medical text stop words list to obtain the clinical information table and disease information table with removal of the stop words;

Step 4, obtaining a patient chief complaint by way of voice or text;

Step 5, removing the stop words from the patient chief complaint to obtain keywords of the text chief complaint;

Step 6, using a fuzzy matching algorithm and the medical data index to fuzzily match the keywords of the text chief complaint and the clinical information table and disease information table with removal of the stop words so as to obtain a preliminary disease diagnosis result;

Step 7, performing a correlation estimation on the preliminary disease diagnosis result to obtain a scoring result, intelligently sorting the scoring result to obtain a sorting result, and taking the top N pieces of data from the sorting result as a disease diagnosis result;

Step 8, performing an optimization decision on the disease diagnosis result to obtain a decision result, and generating reminder information for supplementing the chief complaint according to the decision result;

Step 9, selecting the matched disease number, disease name, department number and disease profile from the disease information table by use of the medical data index according to the disease diagnosis result, and obtaining the doctor name and the hospital from the doctor information table according to the department number so as to obtain a number of treatment doctors; and Step 10, scoring and sorting the number of the treatment doctors, selecting the top M treatment doctors in ranking as a medical guide result, and then sending the disease diagnosis result, the medical guide result and the reminder information together to the mobile medical terminal, so as to assist the patient to perform self-helped disease examination and medical guide in the mobile environment, thereby better promoting the development of the mobile medical technology.

What is claimed is:

1. A mobile health intelligent medical guide system, comprising:
  a mobile device serving as an embedded mobile medical terminal, the mobile medical terminal having a first interface;
  a personal computer having a second interface and a keyboard; and
  a mobile medical cloud server having a third interface connected to the first interface and the second interface, wherein the mobile device and the personal computer are in parallel connections to the mobile medical cloud server; the personal computer is directly connected with the mobile medical cloud server; and the mobile device is connected to the mobile medical cloud server through the first interface over a network;
  wherein each of the mobile medical terminal and the personal computer comprises:
  a voice recognition module; and
  a text entry module, wherein
    the voice recognition module is configured to acquire a patient voice chief complaint, convert the patient voice chief complaint into a text chief complaint, and then send the text chief complaint to the mobile medical cloud server through the third interface, and
    the text entry module is configured to input the text chief complaint through the keyboard and send the text chief complaint to the mobile medical cloud server through the third interface;
  wherein the mobile medical cloud server comprises:
  a medical knowledge base;
  a knowledge reasoning module and a data management module, wherein:
    the knowledge reasoning module is configured to receive the text chief complaint and use the medical knowledge base to perform knowledge reasoning to the text chief complaint to obtain a first disease diagnosis result and a decision result;
    the medical knowledge base comprises a medical data index, a clinical information table, a disease information table, a doctor information table and a department information table, wherein:
      the clinical information table comprises electronic medical records and medical image data;
      the disease information table comprises a disease number, a disease name, a department number, a disease profile, a clinical presentation and a treatment;
      the medical data index is an index established for the disease information table and the clinical information table;
      the doctor information table comprises a doctor number, a doctor name, a hospital, a department number and a professional good; and
      the department information table comprises a department number, a department name and a disease number;
    the knowledge reasoning module comprises a medical text word segmentation processor, a medical text stop words list, a fuzzy matching processor, an intelligent sorting processor, and an optimization decision processor including an optimal rule set, wherein
    the medical text word segmentation processor performs word segmentation on the information in the clinical information table and the disease information table to obtain the clinical information table and the disease information table with performance of the word segmentation;
    the mobile medical cloud server removes stop words from the clinical information table and the disease information table with performance of the word segmentation based on the medical text stop words list to obtain the clinical information table and the disease information table with removal of the stop words;
    the mobile medical cloud server removes the stop words from the text chief complaint based on the medical text stop words list, thereby obtaining keywords of the text chief complaint;
    the fuzzy matching processor uses a fuzzy matching algorithm and the medical data index to fuzzily match the keywords of the text chief complaint and the clinical information table and the disease information table with removal of the stop words so as to obtain the first disease diagnosis result;
    the intelligent sorting processor performs a correlation estimation on the first disease diagnosis result to obtain a scoring result through a TF-IDF algorithm, intelligently sorts the scoring result to obtain a sorting result, and takes top N pieces of data from the sorting result as a second disease diagnosis result, wherein implementation steps of applying the TF-IDF algorithm are as follows:
    (1) for keyword ti of the patient chief complaint, its term frequency (TF) is:

$$tf_{i,j} = \frac{n_{i,j}}{\sum_i n_{k,j}},$$

wherein ni, j is the number of occurrence of the keywords in diagnosis result dj, and the denominator is a sum of the number of occurrence of all words in the diagnosis result dj;
    2) for the keyword ti of the patient chief complaint, its inverse document frequency (IDF) is:

$$idf_i = \log \frac{|D|}{|\{j : t_i \in d_j\}|},$$

wherein |D| represents the total number of diseases in the electronic medical records of the clinical information table and the disease information table, and |j:ti∈dj| represents the number of diseases of the first diagnosis result, and if the number of the diseases of the first diagnosis result is 0, it is expressed as 1+|j:ti∈dj|;
    3) correlation of the keyword ti in the diagnostic result dj is: tfidfi, j=tfi, j×idfi; and 4) result of correlation scoring is sorted in a descending order and the top N pieces of data are taken as the second disease diagnosis result;

the optimization decision processor performs an optimization decision on the second disease diagnosis result by use of the optimal rule set, and if the second disease diagnosis result satisfies any one of rules of the optimal rule set, the second disease diagnosis result is optimal, and thus the decision result is "True"; otherwise, the second disease diagnosis result is not optimal, and thus the decision result is "False"; and the data management module matches a corresponding treatment doctor from the medical knowledge base according to the second disease diagnosis result so as to generate a medical guide result and feeds back the medical guide result to the mobile medical terminal through the third interface; and generates reminder information for supplementing the chief complaint according to the decision result.

2. The mobile health intelligent medical guide system according to claim 1, wherein the data management module comprises:

a data extraction module configured to select a matched disease number, disease name, department number and disease profile from the disease information table by use of the medical data index according to the disease diagnosis result; and obtain the doctor name and the hospital from the doctor information table according to the department number so as to obtain a number of treatment doctors; and a doctor scoring module configured to score and sort the number of the treatment doctors, and select the top M treatment doctors in ranking as the medical guide result.

3. A mobile health intelligent medical guide system for assisting a patient to diagnose medical conditions and a healthcare provider to deliver mobile diagnoses and treatments to the patient in a mobile environment, comprising:

a medical cloud server; and a mobile medical terminal connected to the medical cloud server via a network, and configured to assist a patient to diagnose medical conditions and receive mobile diagnoses and treatments from doctors via the network;

wherein the mobile medical cloud server comprises:

a medical knowledge database including (i) a clinical information table comprising electronic medical records and medical image data; (ii) a disease information table comprising a disease number, a disease name, a department number, a disease profile, a clinical presentation and a treatment; (iii) a medical data index for the clinical information table and the disease information table; (iv) a doctor information table comprising a doctor number, a doctor name, a hospital, a department number and a professional reputation; and (v) a department information table comprising a department number, a department name and a disease number;

a knowledge reasoning module including (i) a medical text word segmentation processor configured to perform word segmentation including removal of stop words from keywords input by the patient from the mobile medical terminal based on a medical text stop words list; (ii) a fuzzy matching processor configured to fuzzily match the input keywords and the clinical information table and the disease information table with removal of stop words so as to obtain a preliminary diagnosis result; (iii) an intelligent sorting processor configured to perform a correlation estimation on the preliminary diagnosis result to obtain a scoring result and intelligently sort the scoring result to obtain a final diagnosis result; and (iv) an optimization decision processor configured to optimize the final diagnosis result based on an optimal rule set; and a data management module configured to match a corresponding treatment doctor from the medical knowledge database according to the final diagnosis result so as to generate and transmit a medical guide result to the mobile medical terminal via the network, so as to assist the patient to perform self-help medical examination, diagnosis and treatment in the mobile environment.

4. The mobile health intelligent medical guide system according to claim 3, wherein the mobile medical terminal is a terminal application installed on a mobile terminal selected from one of a mobile device, a table personal computer (PC), and a hospital medical guide desk.

5. The mobile health intelligent medical guide system according to claim 3, wherein the data management module is further configured to generate reminder information according to the optimal decision result, wherein if the optimal decision result is "True", the reminder information "diagnosis ends" is generated, and if the optimal decision result is "False", the reminder information "in order to improve the accuracy, please supplement the chief complaint information" is generated; and send the disease diagnosis result, the medical guide result and the reminder information together to the mobile medical terminal.

6. The mobile health intelligent medical guide system according to claim 3, wherein the mobile medical terminal comprises:

a voice recognition module configured to recognize an audio indicative of the input keywords from the patient, convert the audio into text, and then send the text indicative of the input keywords to the mobile medical cloud server via the network; and a text entry module configured to permit the patient to manually input the text indicative of the input keywords from the patient and send the text to the mobile medical cloud server via the network.

7. The mobile health intelligent medical guide system according to claim 3, wherein the intelligent sorting processor obtains the final diagnosis result through a TF-IDF algorithm, including:

(1) for a keyword ti of the input keywords from the patient, its term frequency (TF) is:

$$tf_{i,j} = \frac{n_{i,j}}{\sum_i n_{k,j}},$$

wherein ni, j is the number of occurrence of the keywords in the diagnosis result dj, and the denominator is a sum of the number of occurrence of all words in the diagnosis result dj;

2) for the keyword ti of the input keywords from the patient, its inverse document frequency (IDF) is:

$$idf_i = \log\frac{|D|}{|\{j : t_i \in d_j\}|},$$

wherein |D| represents the total number of diseases in the electronic medical records of the clinical information table and the disease information table, and |j:ti∈dj| represents the number of diseases of the first diagnosis result, and if the number of the diseases of the preliminary diagnosis result is 0, it is expressed as $1+|j:t_i \in d_j|$;

3) correlation of the keyword ti in the diagnostic result dj is: tfidfi, j=tfi, j×idfi; and 4) result of correlation scoring is sorted in a descending order and the top N pieces of data are taken as the final diagnosis result.

8. The mobile health intelligent medical guide system according to claim 3, wherein the data management module comprises:

a data extraction module configured to select a matched disease number, disease name, department number and disease profile from the disease information table by use of the medical data index according to the disease diagnosis result; and obtain the doctor name and the hospital from the doctor information table according to the department number so as to obtain a number of treatment doctors; and a doctor scoring module configured to score and sort the number of the treatment doctors, and select the top M treatment doctors in ranking as the medical guide result.

9. The mobile health intelligent medical guide system according to claim 8, wherein the mobile medical terminal is a terminal application installed on a mobile terminal selected from one of a mobile device, a table personal computer (PC), and a hospital medical guide desk.

* * * * *